United States Patent [19]

Farng et al.

[11] Patent Number: 5,002,674

[45] Date of Patent: Mar. 26, 1991

[54] MULTIFUNCTIONAL LUBRICANT ADDITIVES AND COMPOSITIONS THEREOF

[75] Inventors: Liehpao O. Farng, Lawrenceville; Andrew G. Horodysky, Cherry Hill, both of N.J.

[73] Assignee: Mobil Oil Corporation, Fairfax, Va.

[21] Appl. No.: 381,872

[22] Filed: Jul. 19, 1989

[51] Int. Cl.$^5$ ............................................. C10M 105/08
[52] U.S. Cl. ................................................. 252/32.7 E
[58] Field of Search ..................................... 252/32.7 E

[56] References Cited

U.S. PATENT DOCUMENTS 4,648,985  3/1987  Thorsell .................... 252/32.7 E

OTHER PUBLICATIONS

CA 99(10):81660j.
CA 91(5):39568v.
CA 90(7):54502s.
CA 110(25):231727y.
CA 93(16):160599a/AMD.

Primary Examiner—Jacqueline V. Howard
Attorney, Agent, or Firm—A. J. McKillop; C. J. Speciale; H. M. Flournoy

[57] ABSTRACT

Ashless thiophosphates derived from dihydrocarbyl dithiocarbamates have been found to be effective antioxidant/antiwear multifunctional additives for lubricants.

26 Claims, No Drawings

MULTIFUNCTIONAL LUBRICANT ADDITIVES AND COMPOSITIONS THEREOF

BACKGROUND OF THE INVENTION

This invention relates to multifunctional antiwear-/antioxidant additives and to compositions comprising lubricants, greases and other solid lubricants thereof containing a minor amount of an ashless thiophosphate slat derived from a dithiocarbamate.

The metal surfaces of machinery or engines operate under heavy or normal loads wherein the metal is under friction, even when being lubricated. Thus, there is always metal wear which in some cases can be excessive. It is clear that lubricants used to protect the metal surfaces do not completely prevent wear at the points of metal to metal contact. Consequently, the performance of the machine or engine will suffer, and in aggravated cases the machine or engine may be become completely inoperative from the wear caused by the friction and the load.

There have been many attempts to devise additive systems to improve the extreme pressure/load carrying properties of a lubricant. The non-metallic derivatives of the present invention provide lubricating oil compositions with enhanced antioxidant/antiwear and extreme pressure/load carrying characteristics and are believed to be capable of overcoming some of the aforementioned deficiencies of prior art additives.

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation leads to a loss of lubrication properties, and in especially severe cases this may cause complete breakdown of the device being lubricated. Many additives have been tried, however, many of them are only marginally effective except at high concentrations. Improved antioxidants are clearly needed.

Antioxidants or oxidation inhibitors are used to minimize the effects of oil deterioration that occur when, for example, hot oil is contacted with air. The degree and rate of oxidation will depend on temperature, air and oil flow rates and, of particular importance, on the presence of metals that may catalytically promote oxidation. Antioxidants generally function by prevention of chain peroxide reaction and/or metal catalyst deactivation. They prevent the formation of acid sludges, darkening of the oil and increases in viscosity due to the formation of polymeric materials.

Water (moisture) is another critical problem. In spite of even extraordinary precautionary efforts water is found as a film or in minute droplets in vessels containing various hydrocarbon distillates. This brings about ideal conditions for corrosion and damage of metal surfaces of the vessels and the materials contained therein. Also in the lubrication of internal combustion engines, for example, quantities of water are often present as a separate phase within the lubricating system. Another serious problem in respect to metallic surfaces in contact with adjacent metallic surfaces is the surface wear caused by the contact of such surfaces. One material capable of simultaneously coping with such problems effectively is highly desireous.

The use of metal dithiocarbamates (such as zinc, nickel, or lead dialkyl dithiocarbamates) are known as effective antioxidants and antiozonants for many rubbers and polymers in various kinds of applications, such as styrene butadiene rubber and acrylonitrile butadiene rubber.

SUMMARY OF THE INVENTION

This application is directed to lubricant compositions containing small additive concentrations of N,N-dialkyl dithiocarbamate-derived thiophosphates which possess good antioxidant properties coupled with excellent antiwear and extreme pressure load carrying activities. Both the dithiocarbamate moiety and the thiophosphate moiety are believed to provide the basis for the synergistic antiwear activity. The dithiocarbamate group is also believed to contribute significant antioxidant property to these novel additives.

All of these beneficial properties are believed to be enhanced as a result of this novel internal synergism. This unique internal synergism concept is believed to be applicable to similar structures containing (a) dithiocarbamate groups, (b) thiophosphate groups within the same molecule. The products of this patent application show good stability and compatibility when used in the presence of other commonly used additives in lubricant compositions.

The lubricant compositions described herein are believed to be novel and their use as antioxidant/antiwear and extreme pressure/load carrying lubricant additives is also believed to be novel.

DESCRIPTION OF SPECIFIC EMBODIMENTS

The metal dihydrocarbyl dithiocarbamates are synthesized by reacting equal molar amounts of alkali metal hydroxide, a secondary dihydrocarbyl amine, and carbon disulfide in aqueous media or organic solution depending on conditions (Equation 1).

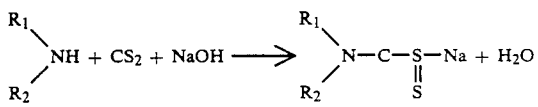

Similarly, triethylammonium salts of dithiocarbamates can be made by reacting triethylamine, dialkylamine and carbon disulfide in non-aqueous media (Equation 2).

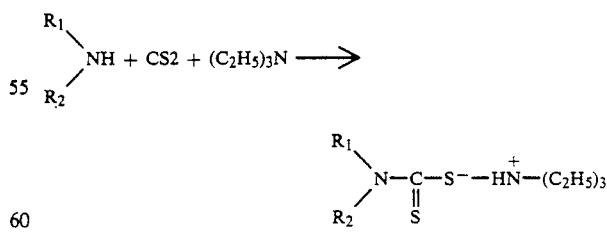

Diethyl chlorothiophosphate (or diethyl phosphorochloridothionate, DEPCT, commercially available from ICI Americas, and Ethyl Corp.) was reacted with either sodium dialkyl dithiocarbamates or triethyl ammonium slats of dialkyl dithiocarbamates to form N,N-dialkyl dithiocarbamate-derived organic thiophosphates as generally described below (Equation 3).

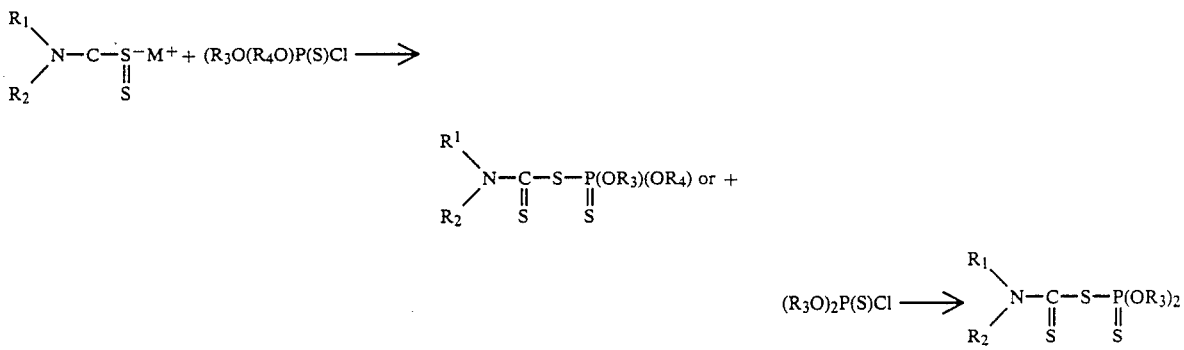

where $M^+$ represents the cationic moiety of the dithiocarbamate salt, such as sodium ion ($Na^+$), trihydrocarbyl ammonium such as triethylammonium ion [$(C_2H_5)_3N^+H$], or other suitable cations. $R_1$ and $R_2$ are hydrogen or $C_1$ to $C_{60}$ hydrocarbyl, at least one of which must be hydrocarbyl.

Other dihydrocarbyl halothiophosphates with the general structure below are also available for these types of reactions.

where X are halides (CL, Br, I)

$R_3$, $R_4$ are hydrogen, or $C_1$ to $C_{60}$ hydrocarbyl, preferably $C_2$–$C_{10}$ alkyl.

An excess of one reagent or another can be used. However, the preferred stoichiometry is approximately one mole of dithiocarbamate salts to approximately one mole of dihydrocarbyl halothiophosphates under ambient conditions with or without a solvent for up to 24 hrs or more.

The general reaction conditions may nevertheless be any suitable conditions known in the art. Usually reaction (1) is preferably carried out at temperatures ranging from about $-20°$ to about $150°$ C., and in molar quantities ranging from less than molar to substantially molar amounts of amine to sulfide to hydroxide and reaction (2) at temperatures of from about $-20°$ to about $200°$ C. If a solvent is used the temperature of reaction will vary accordingly. Usually atmospheric or ambient pressure is used, however, higher or lower pressures may be used if desired. The time of reaction will, or course, vary primarily with the temperature and pressure etc. used.

The base lubricants which are useful with the additives of this invention may be any oil of lubricating viscosity, whether natural, i.e., mineral, or synthetic.

The additives may be therefore incorporated into any suitable lubricating media which comprises oils of lubricating viscosity, e.g., mineral or synthetic; or mixtures of mineral and synthetic or greases in which the aforementioned oils are employed as a vehicle or into such functional fluids as hydraulic fluids, brake fluids, power transmission fluids and the like. In general, mineral oils and/or synthetic, employed as the lubricant oil, or grease vehicle may be of any suitable lubricating visocosity range, as for example, from about 45 SSU and 100° F. to about 6000 SSU at 100° F., and, preferably, from about 50 to about 250 SSU at 210° F. These oils may have viscosity indices from about 70 to about 95 preferred. The average molecular weight of these oils may range from about 250 to about 800. Where the lubricant is to be employed in the form of a grease, the lubricating oil is generally employed in an amount sufficient to balance the total grease composition, after accounting for the desired quantity of the thickening agent and other additive components to be included in the grease formulation. When high temperature stability is not a requirement of the finished grease, mineral oils have a viscosity of at least 40 SSU at 150° F., and particularly those falling within the range from about 60 SSU to about 6,000 SSU at 100° F. may be employed.

In instances where synthetic oil, or synthetic oils are employed as the vehicle for the grease in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylolpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis (p-phenoxy phenyl) ether, phenoxy phenylethers, etc.

Fully formulated lubricating oils may also include a variety of additives (for their known purpose) such as dispersants, detergents, inhibitors, antiwear agents, antioxidant, antifoam, viscosity index improvers, antirust, pour depressant and other additives including phenates, sulfonates, succinimides, sulfurized olefins and zinc dithiophosphates.

The lubricating vehicles of the improved greases of the present invention, containing the above described additives, are combined with a grease forming quantity of a thickening agent. For this purpose, a wide variety of materials may be dispersed in the lubricating vehicle in grease-forming quantities in such degree as to impart to the resulting grease composition the desired consistency. Exemplary of the thickening agents that may be employed in the grease formulation are non-soap thickeners, such as surface-modified clays and silicas, aryl ureas, calcium complexes and similar materials. In general, grease thickners may be employed which do not melt and dissolve when sued at the required temperature within a particular environment; soap thickeners such as metallic (lithium or calcium) soaps including hydroxy stearate and/or stearate soaps can be used however, in all other respects, any material which is normally employed for thickening or gelling hydrocarbon fluids or forming greases can be used in preparing the aforemetnioned improved greases in accordance with the present invention.

Included among the preferred thickening agents are those containing at least a portion of alkali metal, alkaline earth metal or amine soaps of hydroxyl-containing fatty acids, fatty glycerides and fatty esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

Other thickening agents include salt and salt-soap complexes such as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

As has been disclosed hereinabove, the reaction products are useful as multifunctional antiwear/antioxidant-/extreme pressure agents. They are added to the lubricating medium in amounts sufficient to impart such properties to the lubricant. More particularly, such properties will be imparted to the lubricant by adding from about 0.001% to about 10% by weight, preferably from about 0.01% to about 3%, of the neat product.

Having described the invention in general terms, the following specific examples are offered for purposes of illustration no intention to limit the invention is to be inferred therefrom.

EXAMPLE 1

The Preparation of Triethylammonium Salt of N,N-Dicoco Dithiocarbamate

Approximately 385.0 g of dicocoamine (obtained commercially form Armak Chemicals - Akzo Chemie America, 1.0 mole), 600 ml toluene, and 101.3 g of triethylamine (1.0 mole), were mixed together in a three-liter, four-neck reactor equipped with thermometer, Dean-Stark trap condenser, agitator, and dropping funnel. Slowly, 79.6 g of carbon disulfide (1.05 mole) was added dropwise through the dropping funnel to the stirred reactants over a course of one hour. The reaction exotherm was controlled by using an ice-water bath for cooling and the reaction temperature was maintained below 40° C. At the end of the addition, the mixture was further stirred for one additional hour. The toluene solution of dithiocarbamate slat weighed 997 g.

EXAMPLE 2

The preparation of Sodium N,N,-Di-2-Ethylhexyl Dithiocarbamate

Approximately 484 g of di-2-ethylhexylamine (2.0 moles), 500 ml toluene, and 160 g of sodium hydroxide solution (50% w/w, 2.0 moles) were charged in a two-liter, four-neck flask. Slowly, 160 g of carbon disulfide (2.105 moles) was added dropwise through a dropping funnel to the agitated reactants over a two-hour period. The resulting exotherm was controlled with an ice-water bath to keep the reaction temperature below 30° C. At the end of the addition, the reaction mixture was gradually heated form 10° C. to 100° C., and water was azeotropically removed from the Dean-Stark condenser trap. Approximately 97 ml of water was collected. It was further diluted with more toluene to make up a total of 1208 g toluene solution of sodium dithiocarbamate.

EXAMPLE 3

The Reaction Product of N,N-Di-2-Ethylhexyl Dithiocarbamate Sodium Salt

A one-quarter portion of the above product of Example 2 (0.5 mole equivalent sodium N,N-di-2-ethylhexyl dithiocarbamate in toluene, 302 g), 400 ml acetone, and 88 gm of diethyl chlorothiophosphate (0.467 mole) were mixed together in a 1-liter Erlenmeyer flask. The reactants were vigorously stirred at ambient temperature over a 24-hour period. The resulting sodium chloride precipitants were filtered off. Then the volatiles (acetone, toluene, etc.) were removed by distillation at reduced pressure to produce about 204.7 g of a viscous, reddish fluid.

EXAMPLE 4

The Reaction Product of N,N-Dicoco Dithiocarbamate Triethylammonium Salt and Diethyl Chlorothiophosphate A one-quarter portion of the product of Example 1 (0.25 mole, 249 g), 400 ml acetone, and 49.6 g diethyl chlorothiophosphate (0.263 mole) were mixed together in a 1-liter Erlenmeyer flask. The reaction mixture was vigorously agitated at ambient temperature over a course of 24 hours. The resulting precipitants (triethylammonium hydrochloride slats) were filtered off and the organic filtrate was concentrated on a rotary evaporator by removing all the volatiles under reduced pressure. The dark-reddish liquid was further purified via a filtration to produce 156 g viscous liquid.

EVALUATION OF PRODUCTS

The products of Examples 3 and 4 were blended into synthetic oils and evaluated by Catalytic Oxidation Test at 325° F. for 40 hours (Table 1); and Catalytic Oxidation Test at 375° F. for 24 hours (Table 2).

The Catalytic Oxidation test may be summarized as follows.

The tests lubricant composition is subjected to a stream of air which is bubbled through the composition at a rate of five liters per hour. Present in the composition are metals commonly used as materials of engine construction, namely:

(a) 15.6 sq. in. of sand-blasted iron wire,
(b) 0.78 sq. in. of polished copper wire.
(c) 0.87 sq. in. of polished aluminum wire, and
(d) 0.167 sq. in. of polished lead surface.

Inhibitors for oil are rated on the basis of prevention of oil deterioration as measured by the increase in acid formation or neutralization number ($\Delta NN$ or $\Delta TAN$) and kinematic viscosity ($\Delta KV$) occasioned by the oxidation. See U.S. Pat. No. 3,682,980 for further details of the test.

TABLE 1

| | Catalytic Oxidation Test (M334-2) 40 Hours at 325° F. | | | |
|---|---|---|---|---|
| Item | Additive Conc. (wt %) | Percent Change In Viscosity $\Delta KV$, % | Change In Acid Number $\Delta TAN$ | Lead Loss, mg |
| Base Oil (ISO VG 680 Synthetic Oils | — | 292.6 | 8.05 | 1.0 |
| Example 3 | 1.0 | 24.6 | 3.21 | 0.1 |

TABLE 1-continued

| | Catalytic Oxidation Test (M334-2) 40 Hours at 325° F. | | | |
|---|---|---|---|---|
| Item | Additive Conc. (wt %) | Percent Change In Viscosity ΔKV, % | Change In Acid Number ΔTAN | Lead Loss, mg |
| Example 4 | 1.0 | 37.3 | 5.04 | 0.1 |

TABLE 2

| | Catalytic Oxidation Test (M334-10) 24 Hours at 375° F. | | |
|---|---|---|---|
| Item | Additive Conc. (wt %) | Percent Change In Viscosity ΔKV, % | Lead Loss, mg |
| Base Oil (ISO VG 680 Synthetic Oils | — | 1201.4 | 1.7 |
| Example 3 | 1.0 | 112.0 | 0.3 |
| Example 4 | 1.0 | 141.3 | 0.1 |

As shown above, the products of this invention show very good antioxidant activity as evidenced by control of increase in acidity, viscosity and lead loss.

The dithiocarbamate-derived thiophosphates were also evaluated for antiwear performance using the Four-Ball Test (Table 3-5).

The Four Ball Wear Test is disclosed, for example, in U.S. Pat. No. 3,423,316. In general, in this test three steel balls of SAE 52100 steel are held in a ball cup. A fourth ball positioned on a rotatable vertical axis is brought into contact with the three balls and is rotated against them. The force with which the fourth is held against the three stationary balls may be varied according to a desired load. The test lubricant is added to the ball cup and acts as a lubricant for the rotation. At the end of the test, the steel balls are investigated for wear scars; the extend of scarring represents the effectiveness of the lubricant as an antiwear agent. Results are also reported as war rates in volume of wear per unit sliding distance per kilogram load. The lower the wear rate, the more effective the lubricant as an antiwear agent.

TABLE 3

| | Four Ball Test | | |
|---|---|---|---|
| | Wear Scar Diameter in MM, 30 Minute Test 60 kg Load | | |
| Item | 2000 rpm 200° F. | 1000 rpm 300° F. | 2000 rpm 300° F. |
| Base Oil (80% Solvent Paraffinic Bright, 20% Solvent Paraffinic Neutral Minerals Oils) | 3.51 | 1.60 | 2.52 |
| 1% of Example 3 in above base of oil | 0.49 | 0.55 | 0.65 |
| 1% of Example 4 in above base of oil | 0.53 | 0.52 | 0.61 |

TABLE 4

| | Four Ball Test |
|---|---|
| Item | Wear Scar Diameter in MM 40 Kg Load, 30 Minute, 1800 rpm & 167° F. |
| Base Oil (80% Solvent Paraffinic Bright, 20% Solvent Paraffinic Neutral Minerals Oils) | 0.66 |
| 1% Example 3 in above base oil | 0.38 |

TABLE 5

| | Four Ball Test |
|---|---|
| Item | Wear Scar Diameter in MM 20 Kg Load, 60 Minute, 1800 rpm & 130° F. |
| Base Oil (80% Solvent Paraffinic Bright, 20% Solvent Paraffinic Neutral Minerals Oils) | 0.84 |
| 1% Example 3 in above base oil | 0.29 |
| 1% Example 4 in above base oil | 0.43 |

As can be seen from the above wear test results, the products described exhibit considerable antiwear acitivity.

The use of additive concentrations of thiophosphates derived form dithiocarbamates in premium quality automotive and industrial lubricants will significantly enhance stability, reduce the wear and extend service life. The novel compositions described in this patent application are useful at low concentrations and do not contain any potentially undersirable metals or cause corrosivity problems. These multifunctional additives can be commercially made by using an economically favorable process which could be readily implemented.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

What is claimed is:

1. An antioxidant/antiwear/extreme pressure/load carrying lubricant composition comprising a major proportion of an oil of lubricating viscosity or grease or other solid lubricant prepared therefrom and a minor amount of an ashless multifunctional antioxidant/antiwear/extreme pressure/load carrying additive product comprising a thiophosphate derived from a dihydrocarbyl dithiocarbamate.

2. The composition of claim 1 wherein said additive product is a N,N-dihydrocarbyl dithiocarbamate-derived organic thiophosphate generally described by the following formulae

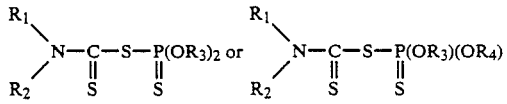

where $R_1$ and $R_2$ are independently $C_1$ to about $C_{60}$ hydrocarbyl and $R_3$ and $R_4$ are independently $C_1$ to about $C_{60}$ hydrocarbyl.

3. The composition of claim 2 wherein said additive is the reaction product of alkali or trihydrocarbylammonium N,N-dihydrocarbyl dithiocarbamate and dihydrocarbyl halothiophosphate.

4. The composition of claim 3 wherein said additive is the reaction product of sodium N,N-di-2-ethylhexyl dithiocarbamate and diethyl chlorothiophosphate.

5. The composition of claim 3 wherein said additive is the reaction product of the triethylammonium salt of N,N-dicoco dithiocarbamate and diethyl chlorothiophosphate.

6. The additive of claim 1 prepared by reacting a dihydrocarbyl dithiocarbamate with a dihydrocarbyl halothiophosphate with the general structure:

where X is halo selected from Cl, Br or I and $R_3$ and $R_4$ are $C_1$ to about $C_{30}$ hydrocarbyl.

7. The composition of claim 6 wherein the materials are reacted in substantially equimolar amounts under ambient conditions for up to 25 hrs or more.

8. The lubricant composition of claim 1 wherein the oil of lubricating viscosity is selected from (1) mineral oils, (2) synthetic oils, (3) mixtures of mineral and synthetic oils or (4) greases prepared from (1), (2) or (3).

9. The lubricant composition of claim 8 wherein the oil is (1) a mineral oil.

10. The lubricant composition of claim 8 wherein the oil is (2) a synthetic oil.

11. The lubricant composition of claim 8 wherein the oil is (3) a mixture of mineral and synthetic oils.

12. The lubricant composition of claim 8 wherein said composition is (4) a grease.

13. The lubricant composition of claim 8 comprising a major amount of said oil and a minor multifunctional amount of from about 0.001 to about 10 wt % of said additive product.

14. An improved process for preparing an additive product of reaction having multifunctional antioxidant-/antiwear/extreme pressure/load carrying lube oil characteristics comprising reacting substantially equimolar amounts of a non-metallic or metallic salt of a dihydrocarbyl dithiocarbamate, an a dihydrocarbyl halothiophosphate under ambient conditions of temperature and pressure or slightly higher temperatures or pressures for a time sufficient to produce said reaction product.

15. The process of claim 14 wherein said dihydrocarbyl dithiocarbamate has the following generalized structure:

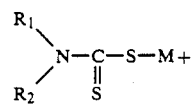

where $R_1$ and $R_2$ are $C_1$ to about $C_{60}$ hydrocarbyl and M+ is the cationic moiety of a dithiocarbamate salt.

16. The process of claim 15 where M+ is selected from alkali metal oins.

17. The process of claim 16 where M+ is $Na^{30}$.

18. The process of claim 15 where M+ is selected from trihydrocarbyl ammonium oins.

19. The process of claim 18 where M+ is a trialkyl ammonium oin.

20. The process of claim 19 where M+ is triethylammonium ion.

21. The process of claim 14 where the dihydrocarbyl halothiophosphate has the following generalized structure:

where X is Cl, Br or I and $R_3$ and $R_4$ are $C_1$ to about $C_{30}$ hydrocarbyl.

22. The process of claim 21 where X is Cl and $R_3$ and $R_4$ are each $C_2H_5$.

23. The process of claim 14 where said additive product is the reaction product of N,N-diethylhexyl dithiocarbamate sodium salt and diethyl chlorothiophosphate.

24. The process of claim 14 where said additive product is the reaction product of N,N-dicoco dithiocarbamate triethylammonium salt and diethyl chlorothiophosphate.

25. A method of providing improved multifunctional antioxidant and antiwear/extreme pressure properties to lubricant compositions comprising blending a minor amount of an additive product consisting of a dithiocarbamate derived organic thiophosphate as described in claim 1 into a major amount of an oil of lubricating viscosity or grease or other solid lubricant prepared therefrom.

26. A method of providing improved fuel economy to internal combustion engines comprising treating the moving parts thereof with a lubricant composition as described in claim 1.

* * * * *

UNITED STATES PATENT AND TRADEMARK OFFICE
CERTIFICATE OF CORRECTION

PATENT NO. : 5,002,674

DATED : March 26, 1991

INVENTOR(S) : Liehpao O. Farng et al.

It is certified that error appears in the above-identified patent and that said Letters Patent is hereby corrected as shown below:

column 9, line 1 patent reads "The additive of claim 1 prepared by" should be --The composition of claim 1 wherein said additive is prepared by-- column 10, line 11 patent reads "$Na^{30}$" should be --$Na^{+}$-- column 10, line 13 patent reads "oins" should be --ions-- column 10, line 15 patent reads "oin" should be -ion--

Signed and Sealed this

Eighteenth Day of August, 1992

*Attest:*

DOUGLAS B. COMER

*Attesting Officer*         *Acting Commissioner of Patents and Trademarks*